US008463619B2

(12) United States Patent
Scarola (10) Patent No.: US 8,463,619 B2
(45) Date of Patent: Jun. 11, 2013

(54) INTEGRATED REAL-TIME AND STATIC LOCATION TRACKING

(75) Inventor: Todd Franklin Scarola, Crozier, VA (US)

(73) Assignee: General Electric Company, Schenectady, NY (US)

( * ) Notice: Subject to any disclaimer, the term of this patent is extended or adjusted under 35 U.S.C. 154(b) by 750 days.

(21) Appl. No.: 12/367,314

(22) Filed: Feb. 6, 2009

(65) Prior Publication Data

US 2010/0204999 A1    Aug. 12, 2010

(51) Int. Cl.
*G06Q 10/00* (2006.01)
(52) U.S. Cl.
USPC ............... 705/2; 705/3; 705/7.19; 340/8.1; 340/438; 340/286.07; 340/573.1; 340/573.4; 235/375
(58) Field of Classification Search
USPC .............. 705/2, 3; 340/8.1, 573.4, 573.1, 340/438, 286.07; 235/375
See application file for complete search history.

(56) References Cited

U.S. PATENT DOCUMENTS

| 4,275,385 | A  | * | 6/1981  | White ............................ 340/8.1 |
| 4,598,275 | A  | * | 7/1986  | Ross et al. .................. 340/573.4 |
| 5,825,283 | A  | * | 10/1998 | Camhi ......................... 340/438 |
| 6,259,355 | B1 | * | 7/2001  | Chaco et al. ............. 340/286.07 |
| 7,080,025 | B2 | * | 7/2006  | Mifune et al. ................ 705/7.19 |
| 7,242,306 | B2 | * | 7/2007  | Wildman et al. .......... 340/573.1 |
| 7,438,216 | B2 | * | 10/2008 | Ambekar et al. ............. 235/375 |
| 2002/0165733 | A1 | * | 11/2002 | Pulkkinen et al. ............... 705/2 |
| 2003/0078810 | A1 | * | 4/2003  | Cole et al. ........................ 705/3 |
| 2004/0243446 | A1 | * | 12/2004 | Wyatt ............................... 705/2 |
| 2005/0035862 | A1 | * | 2/2005  | Wildman et al. .......... 340/573.1 |
| 2006/0282302 | A1 | * | 12/2006 | Hussain ........................... 705/9 |
| 2007/0129983 | A1 |   | 6/2007  | Scherpbier |
| 2007/0239484 | A1 | * | 10/2007 | Arond et al. ..................... 705/2 |
| 2009/0187424 | A1 |   | 7/2009  | Grabowski |
| 2009/0315735 | A1 | * | 12/2009 | Bhavani et al. .......... 340/825.49 |
| 2010/0071044 | A1 |   | 3/2010  | Khan |

FOREIGN PATENT DOCUMENTS

WO    2008/020789 A1    2/2008

OTHER PUBLICATIONS

Google patents search result, Jan. 29, 2013.*
Goolge search result, Jan. 29, 2013.*
GB1001415.7 Search Report under Section 17(5), May 26, 2010.

* cited by examiner

*Primary Examiner* — Dilek B Cobanoglu
(74) *Attorney, Agent, or Firm* — Hanley, Flight and Zimmerman, LLC (57) ABSTRACT

Location tracking systems and techniques are provided. In one embodiment, a system includes a memory device and a processor configured to execute a plurality of routines stored in the memory device. The plurality of routines includes receiving of a plurality of patient locations as provided by a respective plurality of location-providing systems from one or more data sources, determination of a resolved patient location by selecting one of the plurality of patient locations based at least in part on a hierarchy of patient locations, and outputting of the resolved patient location. In some embodiments, the location-providing systems may include a real-time location system and a static location system, which may provide a current location and an assigned location, respectively.

13 Claims, 8 Drawing Sheets

INTEGRATED REAL-TIME AND STATIC LOCATION TRACKING

BACKGROUND

The subject matter disclosed herein relates generally to tracking locations of patients, equipment, and staff in a medical facility and, more particularly, tracking locations of patients, equipment, and staff using more than one location tracking system.

To track locations of patients, equipment, and staff, a medical facility may employ one of many available location tracking systems. Such systems may include a static location system based on the Health Level Seven (HL7) medical communications protocol or a real-time location system (RTLS) that may generate location information in real time. Generally, an HL7-based system may include location assertions entered by medical personnel, such as patient hospital bed assignment. RTLS-generated location information may be provided in real time using any number of real-time tracking methods, such as tracking the location of radio frequency identification (RFID) or infrared (IR) tags associated with patients, equipment, or staff.

Each of the above-described location tracking systems may have limitations. For example, location assertions from an HL7-based system may bear little relation to an actual physical location of a patient for large blocks of time. Using an HL7-based location system, a patient's real location may be unknown between admission and room occupancy, during smoking breaks, or while receiving diagnostic treatment in radiology or other service departments. Moreover, in a busy area such as the emergency department (ED) or operating room (OR), an HL7-based location system may be particularly ineffective as a patient may be frequently moved from place to place. Thus, a patient's location may be completely unknown for hours in such locations, as departmental and admissions/discharge/transfer (ADT) systems may not update a patient's location in a sufficiently rapid manner.

Conversely, RTLS-based location readings may be subject to varying levels of granularity depending on the nature of the RTLS infrastructure in a medical facility. For example, an RTLS-based location reading may indicate that a patient has moved from one department to another, but the real-time tracking signal associated with the patient may be non-specific in certain large areas, such as a post-anesthesia care unit (PACU) or the ED. In particular, an RTLS-location reading may be especially imprecise in areas that include multiple bays and/or curtains separating one patient from another. Under such circumstances, an RTLS-based system may report that a patient is in a given area, but may not report the particular bay or curtain area where the patient is currently situated.

BRIEF DESCRIPTION

Certain aspects commensurate in scope with the originally claimed invention are set forth below. It should be understood that these aspects are presented merely to provide the reader with a brief summary of certain forms various embodiments of the presently disclosed subject matter might take and that these aspects are not intended to limit the scope of the invention. Indeed, the invention may encompass a variety of aspects that may not be set forth below.

Embodiments of the presently disclosed subject matter may generally relate to systems for location tracking in a medical facility. In one embodiment, a system includes a memory device and a processor configured to execute a plurality of routines stored in the memory device. The plurality of routines may effect receiving of a plurality of patient locations as provided by a respective plurality of location-providing systems from one or more data sources, determination of a resolved patient location by selecting one of the plurality of patient locations based at least in part on a hierarchy of patient locations, and outputting of the resolved patient location. In certain embodiments, the location-providing systems may include a real-time location system and a static location system, which may provide a current location and an assigned location, respectively.

In another embodiment, a computer-implemented method for location tracking may include using a processor of a data processing system to receive subject location data that includes static location data from a static subject location system and real-time location data from a real-time subject location system, to determine a resolved subject location, and outputting the resolved subject location. Determining the resolved subject location is based at least in part on the received subject location data and a hierarchy relating possible subject locations to one another. In some embodiments, the subject being located is a patient.

In a further embodiment, a method for location tracking may include ascertaining a static patient location using a static location system and a real-time patient location using a real-time location system, receiving the static and real-time patient locations into a data processing system, and selecting one of the locations as a resolved patient location, and outputting the resolved patient location. Selecting the resolved patient location is based at least in part on a hierarchy of possible patient locations using the data processing system.

Various refinements of the features noted above may exist in relation to various aspects of the subject matter described herein. Further features may also be incorporated in these various aspects as well. These refinements and additional features may exist individually or in any combination. For instance, various features discussed below in relation to one or more of the illustrated embodiments may be incorporated into any of the above-described embodiments of the present disclosure alone or in any combination. Again, the brief summary presented above is intended only to familiarize the reader with certain aspects and contexts of the subject matter disclosed herein without limitation to the claimed subject matter.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments of the presently disclosed subject matter will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Moreover, while the term "exemplary" may be used herein in connection to certain examples of aspects or embodiments of the presently disclosed subject matter, it will be appreciated that these examples are illustrative in nature and that the term "exemplary" is not used herein to denote any preference or requirement with respect to a disclosed aspect or embodiment. Further, any use of the terms "top," "bottom," "above," "below," other positional terms, and variations of these terms is made for convenience, but does not require any particular orientation of the described components.

Figure 1:
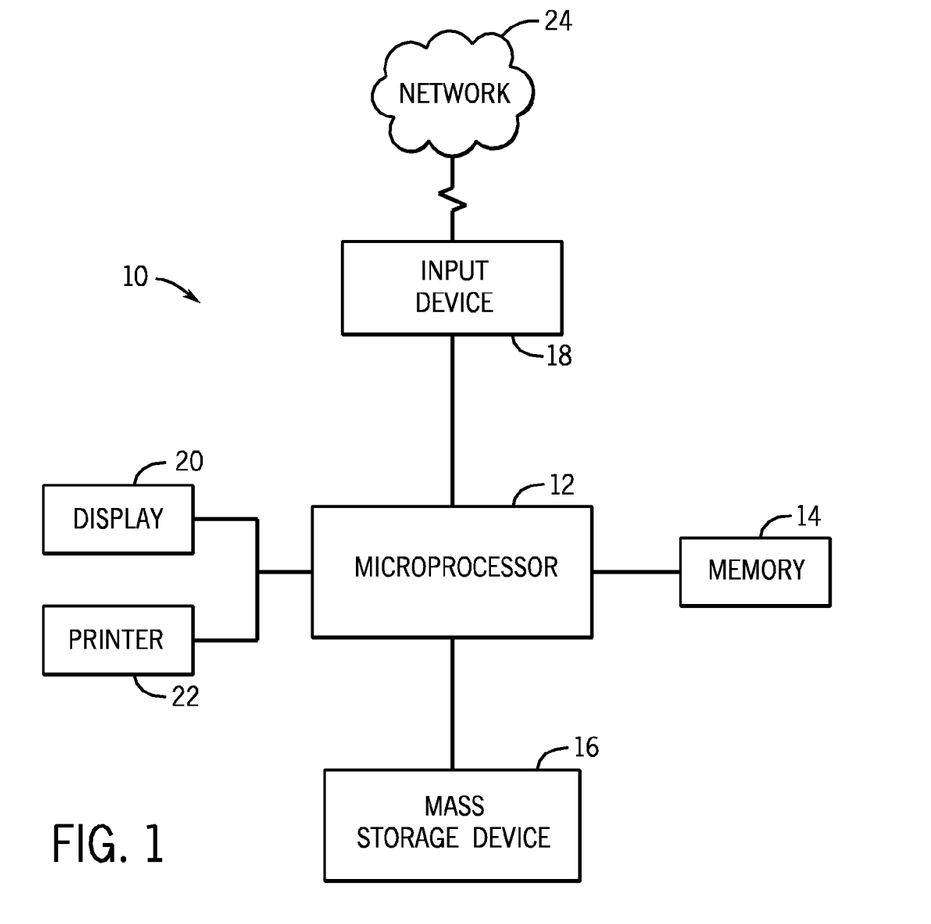
FIG. 1 is a block diagram of an exemplary processor-based device or system in accordance with one embodiment.

Turning now to the drawings, and referring first to FIG. 1, an exemplary processor-based system 10 for use in conjunction with the subject matter described herein is depicted. The exemplary processor-based system 10 may be a general-purpose computer, such as a personal computer, configured to run a variety of software, including software implementing all or part of the functionality described herein. Alternatively, the processor-based system 10 may include, among other things, a mainframe computer, a distributed computing system, or an application-specific computer or workstation configured to implement all or part of the present technique based on specialized software and/or hardware provided as part of the system. Further, the processor-based system 10 may include either a single processor or a plurality of processors to facilitate implementation of the presently disclosed functionality.

In general, the exemplary processor-based system 10 may include a microcontroller or microprocessor 12, such as a central processing unit (CPU), which may execute various routines and processing functions of the system 10. For example, the microprocessor 12 may execute various operating system instructions as well as software routines configured to effect certain processes and stored in or provided by a manufacture including a computer readable-medium, such as a memory 14 (e.g., a random access memory (RAM) of a personal computer) or one or more mass storage devices 16 (e.g., an internal or external hard drive, a solid-state storage device, CD-ROM, DVD, or other storage device). In addition, the microprocessor 12 processes data provided as inputs for various routines or software programs, such as data provided as part of the present techniques in computer-based implementations.

Such data may be stored in, or provided by, the memory 14 or mass storage device 16. Alternatively, such data may be provided to the microprocessor 12 via one or more input devices 18. The input devices 18 may include manual input devices, such as a keyboard, a mouse, or the like. In addition, the input devices 18 may include a network device, such as a wired or wireless Ethernet card, a wireless network adapter, or any of various ports or devices configured to facilitate communication with other devices via any suitable communications network 24, such as a local area network or the Internet. Through such a network device, the system 10 may exchange data and communicate with other networked electronic systems, whether proximate to or remote from the system 10. The network 24 may include various components that facilitate communication, including switches, routers, servers or other computers, network adapters, communications cables, and so forth.

Results generated by the microprocessor 12, such as the results obtained by processing data in accordance with one or more stored routines, may be provided to an operator via one or more output devices, such as a display 20 and/or a printer 22. Based on the displayed or printed output, an operator may request additional or alternative processing or provide additional or alternative data, such as via the input device 18. Communication between the various components of the processor-based system 10 may typically be accomplished via a chipset and one or more busses or interconnects which electrically connect the components of the system 10. Notably, in certain embodiments of the present technique, the exemplary processor-based system 10 may be configured to resolve locations of patient, equipment, or staff by processing location data from multiple location tracking systems.

Figure 2:
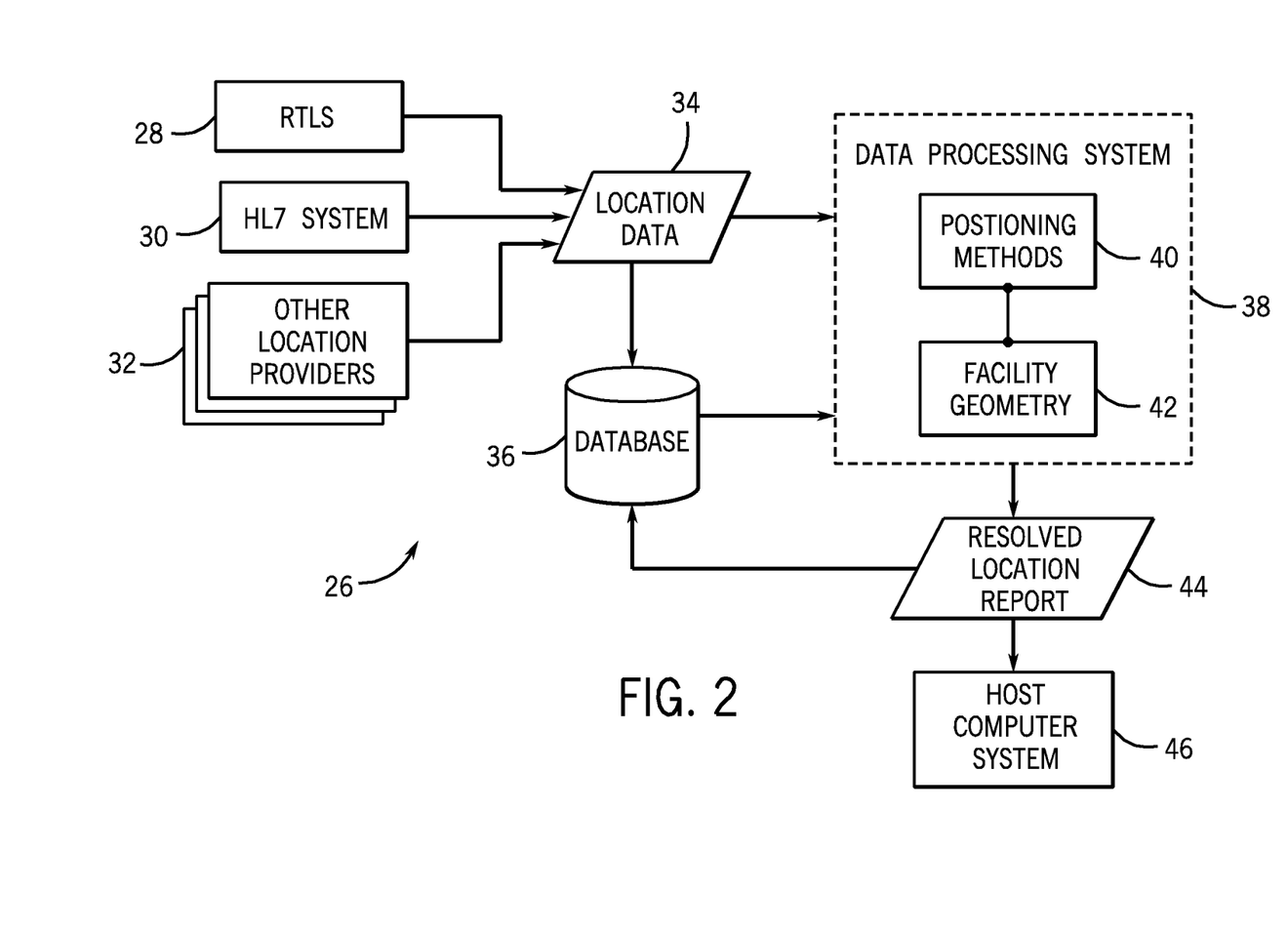
FIG. 2 is a block diagram of an exemplary location tracking system that integrates multiple location tracking systems in accordance with one embodiment.

FIG. 2 illustrates an exemplary system 26 for acquiring and processing location data in accordance with one embodiment. In the system 26, a real-time location system (RTLS) 28, a static Health Level Seven (HL7)-based location system 30, and/or other location providers 32 may each provide location data 34. By way of example, the location data 34 from the RTLS 28 may include a raw data feed of real-time location data and/or location history for one or more radio frequency identification (RFID) or infrared (IR) tags associated with subjects such as patients, equipment, or staff. The location data 34 from the HL7-based system 30 may include an assertion of a patient location. Such assertions of patient location may include, for example, direct-entered manual location assertions or data stream integrated location messages. By way of example, an admissions/discharge/transfer (ADT) system (e.g., a bed placement system) may provide location data 34 indicating a particular bed in which a patient is assigned using the HL7 communications protocol. Other location providers 32 may provide any additional location data 34 to supplement the RTLS 28 and the HL7-based system 30, and may include, for example, a security access system that controls access to locations within the medical facility or a tracking system that employs the Global Positioning System (GPS) for indoor or outdoor tracking of patients, equipment, and/or staff. Generally, the system 26 may obtain location data 34 from at least two location tracking systems, one of which may offer greater accuracy and one of which may offer greater precision. Data structures that define the location data 34 may incorporate notions of "current location" and "assigned location," or such designations may be applied during processing at a later time.

The location data 34 from the multiple location systems 28, 30, and/or 32 may be stored in a database 36 or transmitted to a data processing system 38. Using the location data 34 and/or additional data from the database 36, the data processing system 38 may resolve a precise patient location by selecting the location data 34 that derives from the most precise location system determined to be currently accurate. As discussed with reference to FIGS. 7 and 8 below, the processing performed by the data processing system 38 may include accessing the location data 34; resolving a patient location based on positioning methods 40, facility geometry 42, and a hierarchy of possible locations (described below with reference to FIG. 3); and outputting the resolved patient location.

In the course of resolving the precise patient location, the data processing system 38 may employ rule-based location selection methods, based on positioning methods 40 and facility geometry 42, to interpret a real-time location data 34 feed from the location data 34 provided by the RTLS 28, HL7-encoded location data 34 from the HL7-based system 30, and/or other location data 34 from the other location providers 32. Such methods are described further below with reference to FIGS. 3-8. Interpreting the real-time location data feed may involve mapping such real-time location data to predefined locations in a hierarchy of possible locations in a medical facility. Concurrently, the data processing system 38 may also map static HL7-based location data 34 from the HL7-based system 30 and/or location data 34 from the other location providers 32 to the predefined locations in the hierarchy of possible facility locations. Additionally, the data processing system 38 may designate whether the location data 34 from each system 28, 30, or 32 represents a "current location" or an "assigned location," and/or may prioritize the locations if more than one location is designated as either "current" or "assigned." For example, "current" locations may be prioritized based on likely accuracy, while "assigned" locations may be prioritized based on precision or granularity.

With the location data 34 from the multiple location systems 28, 30, and 32 mapped to a common definition of possible locations, the data processing system 38 may resolve a precise patient location by selecting the most precise, accurate location data 34 based on the hierarchy of possible patient locations. The data processing system 38 may thereafter output a resolved location report 44 indicating the resolved patient location. The resolved location report 44 may be stored in the database 36 or output to a host computer system 46 or a display of the data processing system 38. From the host computer system 46 or the display of the data processing system 38, hospital or medical facility staff may ascertain the best currently-known location of a given patient.

Figure 3:
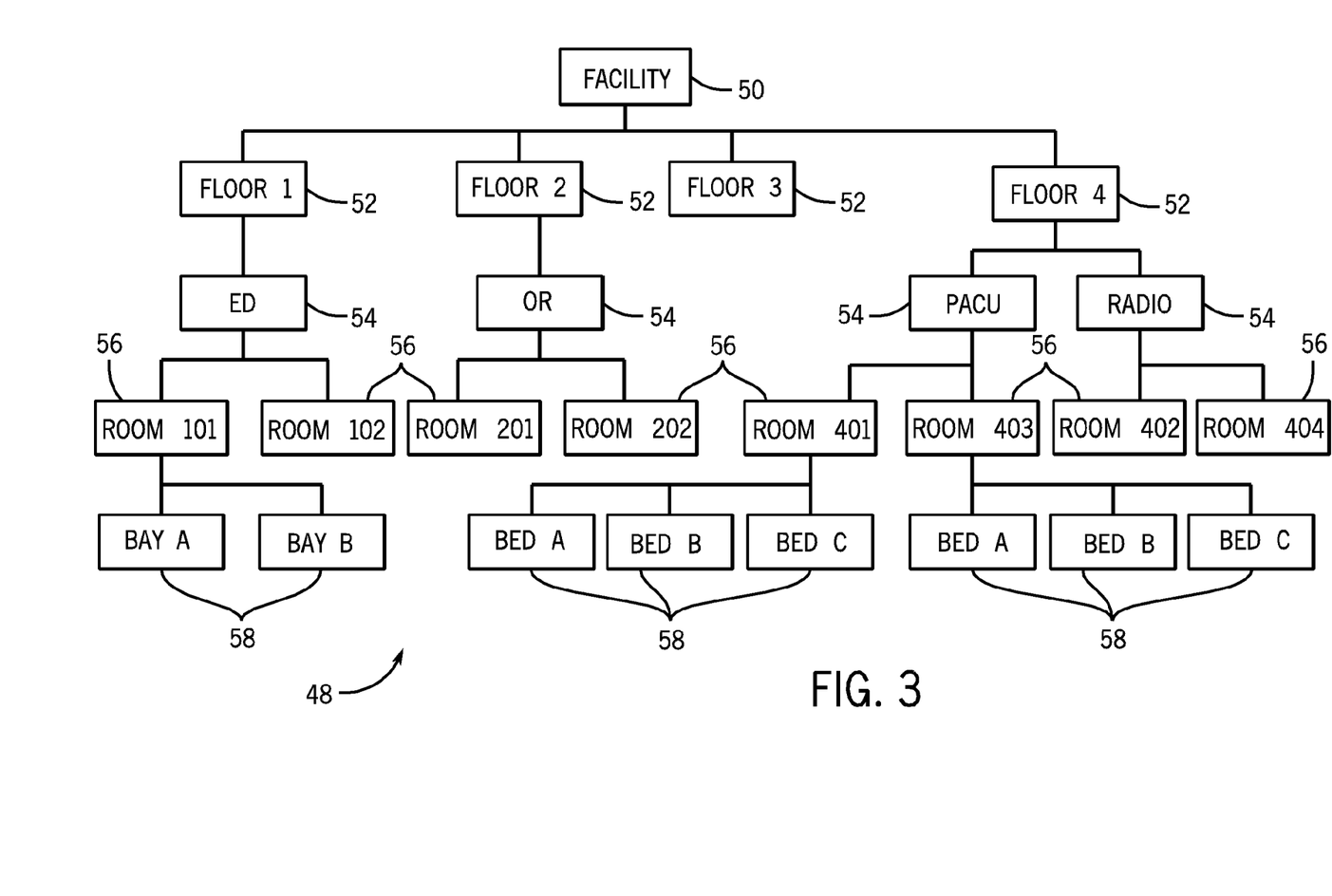
FIG. 3 is a block diagram of an exemplary medical facility location hierarchy for use by the exemplary system of FIG. 2.

FIG. 3 is a block diagram illustrating an exemplary medical facility location hierarchy 48. The medical facility location hierarchy 48 may generally depict all possible locations in a medical facility 50 where patients, equipment, or staff may be tracked using one or more of the location tracking systems 28, 30, or 32. Such a location hierarchy 48 may be employed by the data processing system 38 of the exemplary system 26 to resolve a precise patient location; each of the locations illustrated in the hierarchy 48 may represent a mapping to a location represented by the location data 34 from the various location systems 28, 30, or 32. It should be appreciated that while four sublevels are depicted, the hierarchy 48 may include any number of levels of precision depending on the capabilities of the location tracking systems 28, 30, or 32.

In the exemplary hierarchy 48 of FIG. 3, various predefined locations in the medical facility 50 where patients, equipment, or staff may be tracked are described in a decompositional hierarchical structure. The medical facility 50 may be divided into a series of floors 52, each of which may be divided into one or more departmental areas 54. Each area 54 may be divided into one or more rooms 56, and each room 56 may be further divided into one or more bays or beds 58. As illustrated, some floors 52 may not be divided into areas 54, or areas 54 into rooms 56, etc.

With particular attention to the locations on the fourth floor 52 of the location hierarchy 48, which support an exemplary use to be described below, the fourth floor 52 of the medical facility 50 may include a post-anesthesia care unit (PACU) and a radiology department (RADIO) as departmental areas 54. The PACU may include two rooms 56, each of which may hold three beds 58 labeled A-C. The RADIO may include two rooms 56 that are not further divided. The hierarchy 48 may thus describe the various locations in parent-child relationships. For example, Floors 1-4 are children of the Facility, the PACU and RADIO are children of Floor 1, Rooms 401 and 403 are children of the PACU, and Beds A-C are children of Room 401. As such, in the present hierarchy 48, Bed A of Room 401 of the PACU may be considered a descendant of the medical facility 50, the fourth floor 52, the PACU area 54, and the room 56 where it is located (i.e., Room 401). As should be appreciated, the same Bed A is not a descendant of any other location depicted in the exemplary hierarchy 48.

Figure 4:
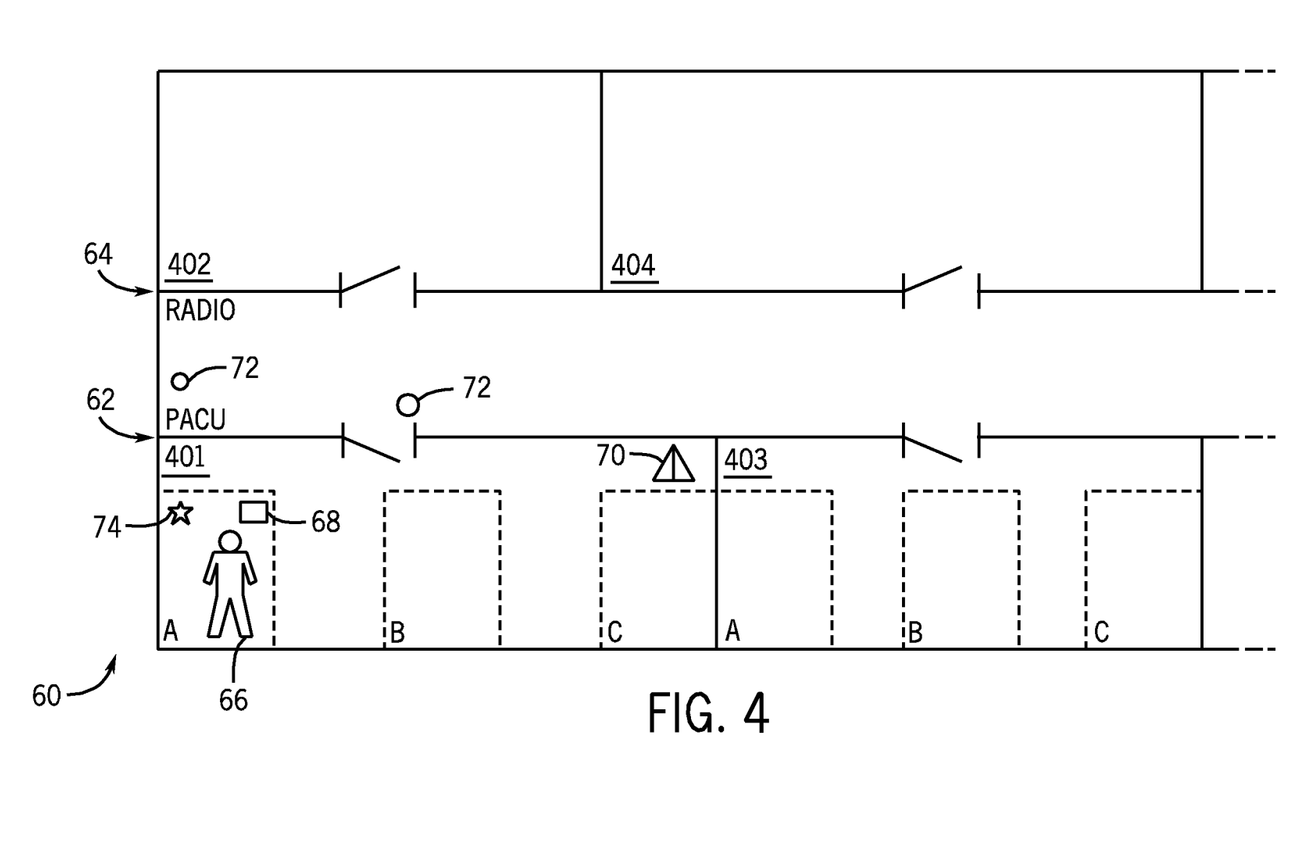
FIG. 4 is a schematic diagram of an exemplary medical facility floor plan illustrating patient tracking using the system of FIG. 2 when the patient is at a first location.
Figure 5:
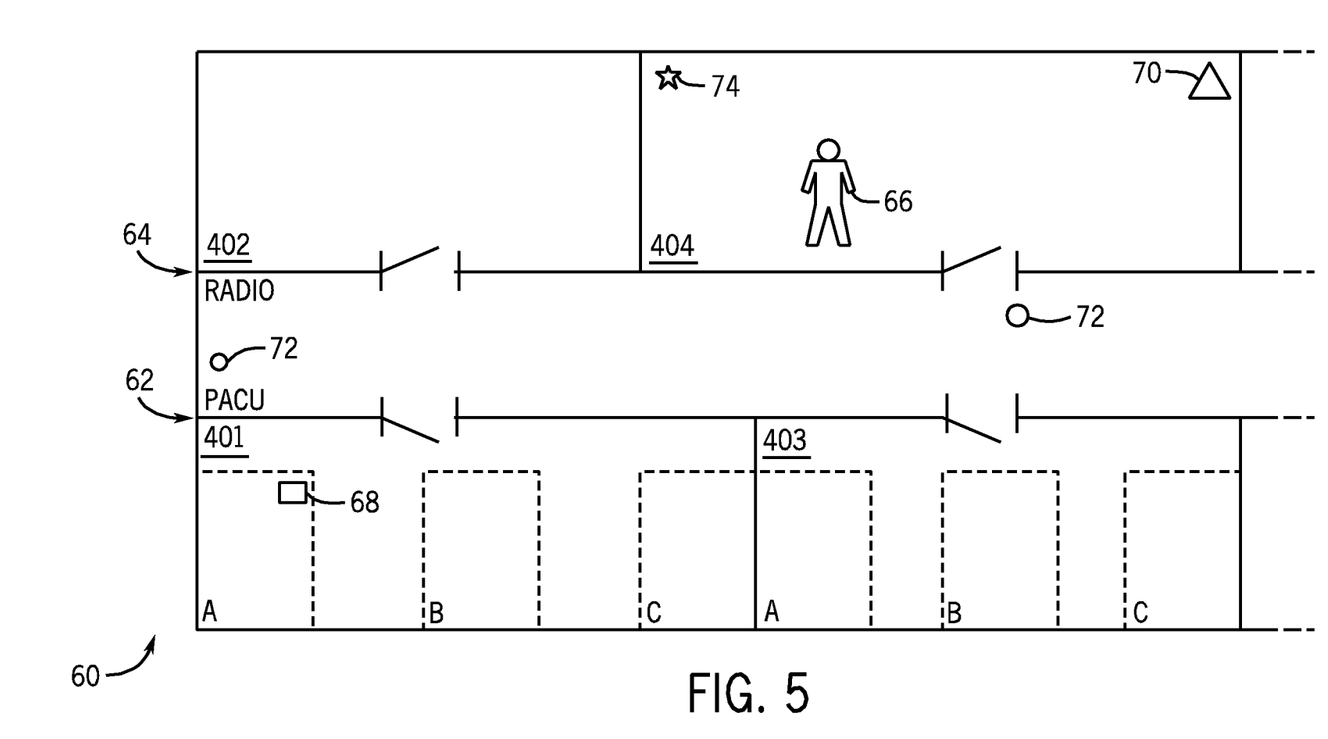
FIG. 5 is a schematic diagram of an exemplary medical facility floor plan illustrating patient tracking using the system of FIG. 2 when the patient is at a second location.

Whether a particular location is a descendent of another may enable the data processing system 38 to determine a most precise, accurate location from among the location data 34; FIGS. 4 and 5 provide one such example. In FIGS. 4 and 5, an exemplary floor plan 60 may include the areas 54 of the fourth floor 52 as illustrated in the exemplary location hierarchy 48 of FIG. 3. In the present example, the areas 54 include a post anesthesia care unit (PACU) 62 and a radiology department (RADIO) 64. Numeral 66 indicates a true patient location, numeral 68 indicates a static location provided by the HL7-based system 30, numeral 70 indicates a real-time location provided by the RTLS 28, numeral 72 indicates an alternative location provided by the other location providers 32, such as a security access system that monitors when the patient 66 enters or exits an access-controlled zone, and numeral 74 indicates a resolved precise patient location as determined by the data processing system 38. In the example of FIGS. 4 and 5, the static location 68 may be designated by the data processing system 38 as an "assigned location," since the static location 68 derives from the HL7-based system 30, while the real-time location 70 may be designated as a "current location," since the real-time location 70 derives from the RTLS 28.

Turning first to FIG. 4, the patient 66 may be actually located in Bed A in Room 401 in the PACU 62. Due to varying accuracy and precision, the location systems 28, 30, and 32 may indicate different locations when the location data 34 is mapped to the hierarchy 48 by the data processing system 38. As illustrated in FIG. 4, the static location 68 indicates that the patient 66 is located in Bed A of Room 401 of the PACU 62. In contrast, the real-time location 70 may indicate that the patient 66 is located in Room 401 of the PACU 62, while the and the alternative location 72 may indicate only that the patient 66 is located PACU 62.

Based on the hierarchy 48, the data processing system 38 may resolve the precise patient location 74 by selecting the most precise, accurate location 68, 70, or 72. In the present example, the static location 68 is a descendant of the real-time location 70 and alternative location 72. Accordingly, no data indicates that the static location 68 is not accurate. Since the static location 68 ("assigned location") is more precise than the real-time location 70 ("current location") and the alternative location 72, the data processing system 38 may select the static location 68 as the resolved precise patient location 74. The resolved patient location 74 may thus indicate that the patient 66 is located in Bed A of Room 401 of the PACU 62, as illustrated in FIG. 4.

Turning next to FIG. 5, if the patient 66 leaves the assigned room, for example, to undergo diagnostic radiology in Room 404 of the RADIO 64, the static patient location 68 may continue to indicate the patient location as Bed A of Room 401 of the PACU 62. However, the real-time location 70 may indicate that the patient 66 is in room 404 of the RADIO 64, while the alternative location 72 may indicate only that the patient 66 is in the RADIO 64, respectively. Because the static patient location 68 ("assigned location") is not a descendent of the real-time patient location 70 ("current location"), the data processing system 38 may determine that the static location 68 is not accurate and, consequently, may select the real-time location 70 as the resolved patient location 74. In this way, the data processing system 38 may choose the most precise accurate location as the resolved patient location 74.

Figure 6:
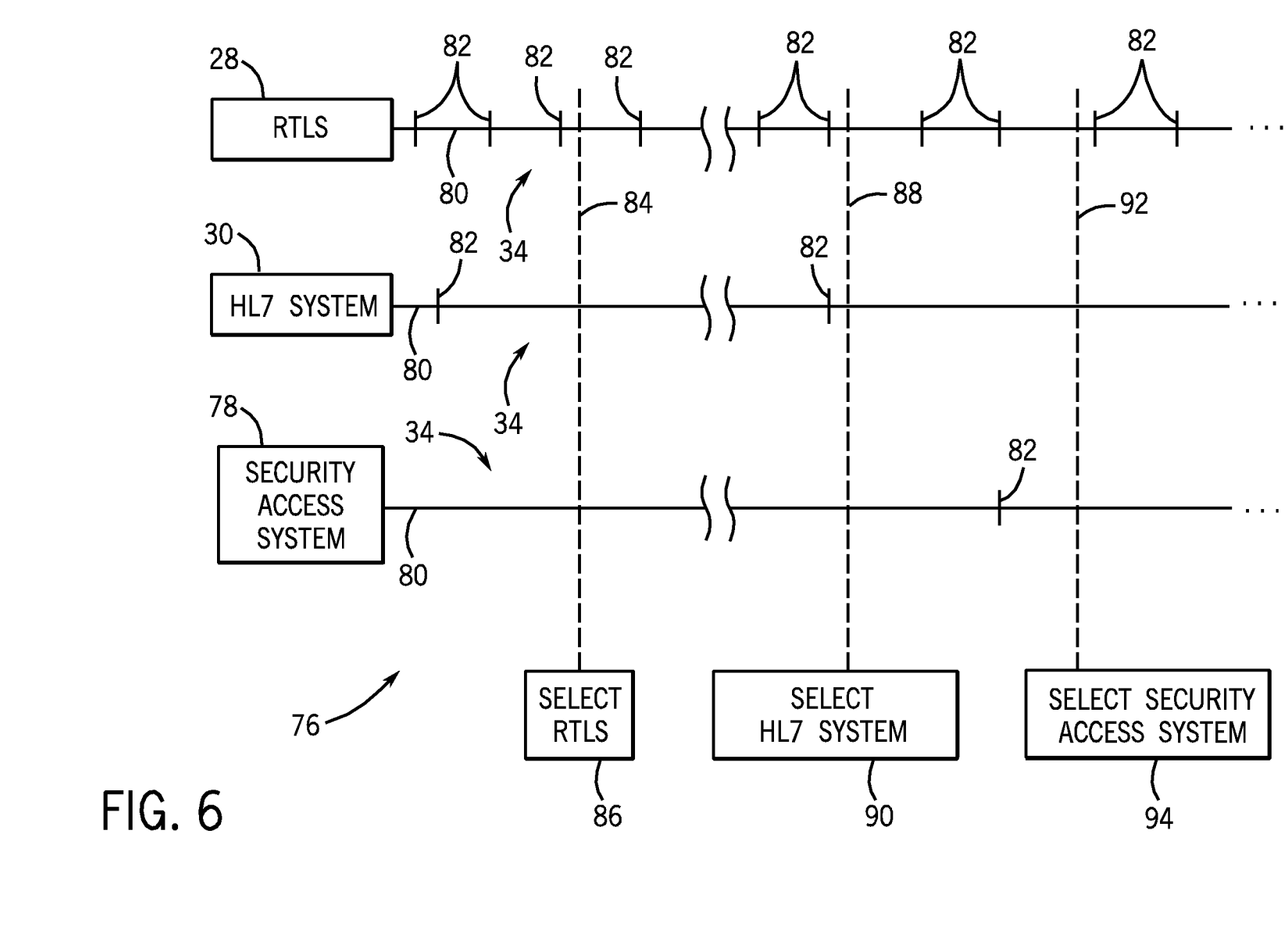
FIG. 6 is a timing diagram illustrating location tracking based on data priority rules in accordance with one embodiment.

FIG. 6 is a timing diagram 76 representing a manner of resolving locations of patients, equipment, or staff in a medical facility by prioritizing the location data 34 based on when the data 34 was last updated. The rules governing the prioritization may vary depending on which location systems 28, 30, or 32 supply the location data 34, as discussed below. Moreover, the prioritization rules may be employed by the data processing system 38 to resolve locations of patients, equipment, and staff alone or in conjunction with a hierarchy of possible locations in the manner described above with reference to FIGS. 3-5.

In the diagram 76, three location systems may provide streams of location data 34 to the data processing system 38, including the RTLS 28, the HL7-based system 30, and a security access system 78, which may represent one of the other location providers 32. Timelines 80 associated with each of the location systems 28, 30, and 78 illustrate when the location data 34 from each system transmits a location update 82 relative to one another. For example, in the exemplary diagram 76, the HL7-based system 30 supplies the first update 82 relative to the other systems 28 and 78, which may represent a point at which a patient is assigned to a bed by an admissions/discharge/transfer (ADT) system. The RTLS 28 may thereafter transmit updates 82 at regular intervals (e.g., every 15-30 seconds), which may represent readings of a radio frequency identification tag on a subject patient, piece of equipment, or medical facility staff member. Updates 82 associated with the security access system 78 may indicate when patients, equipment, or staff enter or exit an access-controlled area (e.g., by swiping a card key or being admitted by facility staff using a card key).

The data processing system 38 may resolve a precise location by selecting location data 34 from either the RTLS 28, the HL7-based system 30, or the security access system 78 based on when the location data 34 was updated, as well as certain characteristics associated with each system 28, 30, or 78. By way of example, the data processing system 38 may select the RTLS 28 location data 34 at a given time 84, as illustrated by numeral 86, if the location data 34 from the RTLS 28 is the most recently updated and the other systems 30 and 78 have not updated within a specified amount of time (e.g., not updated in the last 30 seconds, not updated in the last two minutes, not updated in the last five minutes, etc.). The data processing system 38 may effect the selection 86 because, while the RTLS 28 location data 34 may sometimes be less precise, the RTLS 28 location data 34 may often be more reliable, since the location data 34 from the other systems 28 and 78 may become stale. In contrast, at a time 88, the data processing system 38 may select the location data 34 from the HL7-based system 30, as illustrated by numeral 90, because the HL7-based system 30 has been updated within the specified amount of time (e.g., not updated in the last 30 seconds, not updated in the last two minutes, not updated in the last five minutes, etc.). Similarly, at a time 92, the data processing system 38 may select the location data 34 from the security access system 78, as illustrated by numeral 94, because the security access system 78 has been updated recently (e.g., within the last 30 seconds, within the last two minutes, within the last five minutes, etc.). In the event that the HL7-based system 30 and the security access system 78 are updated around the same time, the data processing system 38 may select the system 30 or 78 deemed to be more reliable. In the instant example, the location data 34 from the security access system 78 may be considered more reliable than the HL7-based system, as the use of a security card may be more reliable than a manually-entered location assignment.

Figure 7:
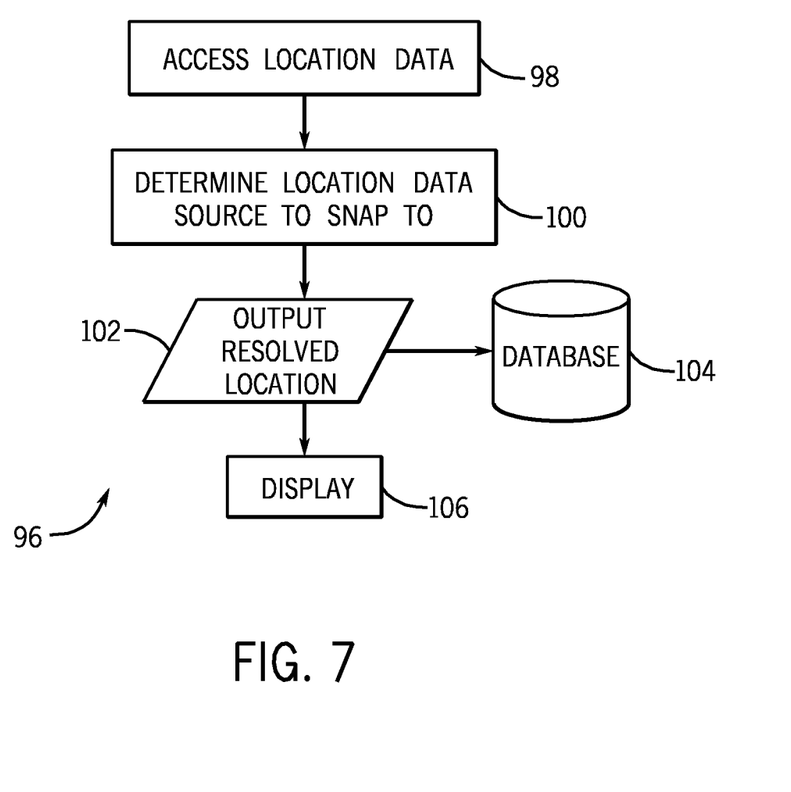
FIG. 7 is a flowchart illustrating a method of performing integrated location tracking using location data from multiple location tracking systems in accordance with one embodiment.

FIG. 7 is a flowchart 96 illustrating a technique to resolve the precise patient location 74 from the location data 34 provided by multiple location systems 28, 30, and/or 32 using the data processing system 38. In a first step 98, the data processing system 38 may access the location data 34 from the location systems 28, 30, and/or 32. In a subsequent step 100, the data processing system 38 may resolve the precise patient location 74 by selecting the location data 34 from among the location systems 28, 30, and/or 32 based on when the location data 34 was updated and/or based on a hierarchy of possible locations. An exemplary manner of performing step 100 to resolve the precise patient location 74 is described below with reference to FIG. 8. Following step 100, the data processing system 38 may output the resolved location in step 102. The output resolved location may be stored in a local or remote database 104, such as within the host computer system 46 or elsewhere within the system 26, or may be sent to an electronic display 106 or printer.

Figure 8:
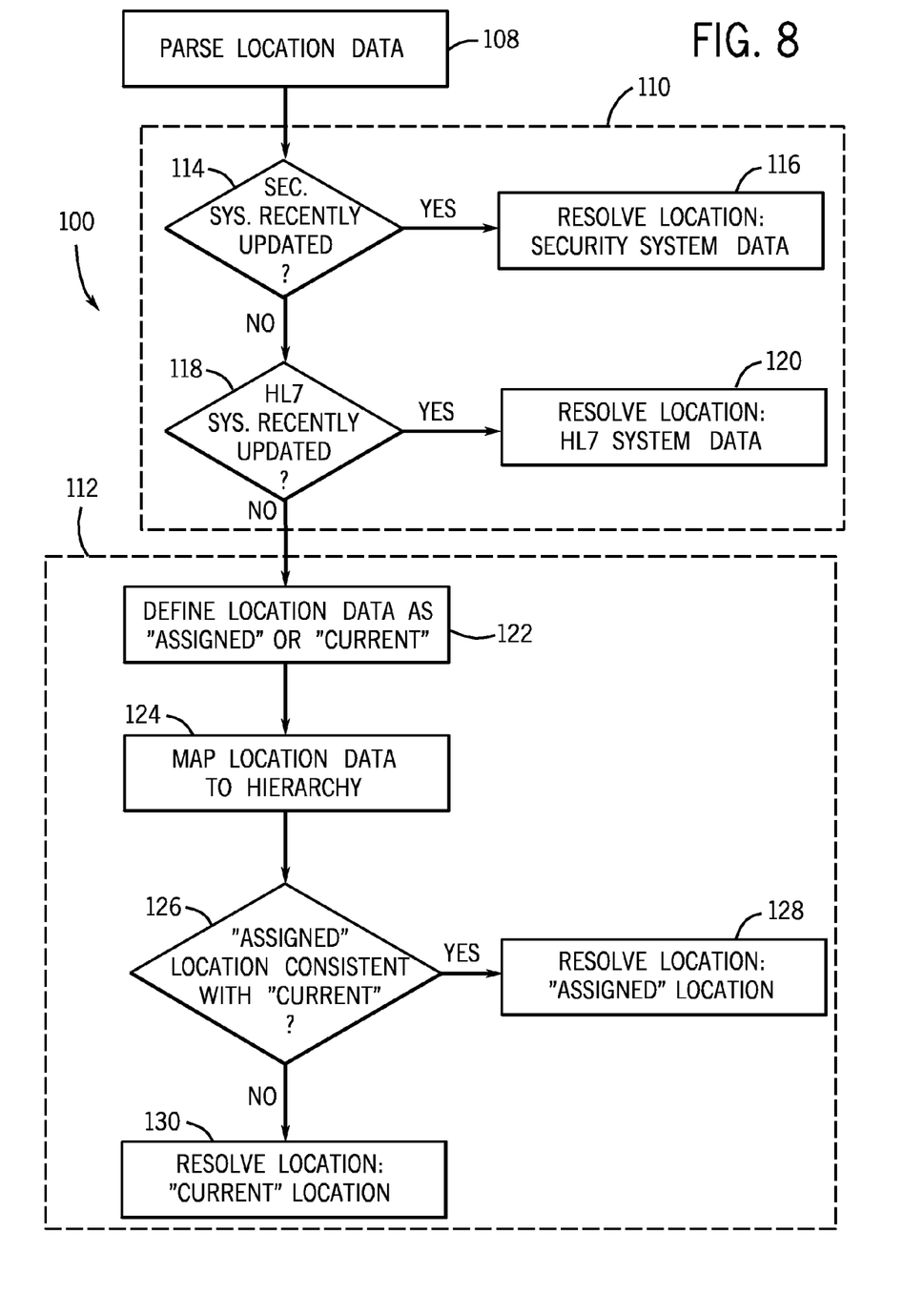
FIG. 8 is a flowchart illustrating a method of resolving a location based on data priority rules and a location hierarchy in accordance with one embodiment.

Turning to FIG. 8, a flowchart illustrates one embodiment of step 100 of FIG. 7 in greater detail. Step 100 may begin with a step 108, in which the data processing system 38 may parse the location data 34 to discern from which system 28, 30, 32 the location data 34 derives and/or to discern when the location data 34 was most recently updated. Subsequently, the data processing system 38 may resolve the precise patient location 74 based on when the location data 34 was updated in a process 110 and/or may resolve the precise patient location 74 based on a hierarchy of possible locations in a process 112. The process 110 generally corresponds to the example of FIG. 6, while the process 112 generally corresponds to the example of FIGS. 3-5.

After the location data 34 has been parsed in step 108, the data processing system 38 may determine whether the most recently updated location data 34 (e.g., location data 34 updated within the previous 30 seconds, within the previous two minutes, within the previous five minutes, etc.) includes location data 34 from systems 32, such as the security access system 78, as illustrated by a decision block 114. If so, in step 116, the data processing system 38 may resolve the precise location of the patient 74 as the location data 34 associated with the security access system 78, since the security access system 78 may be the most reliable source of location data 34 in the short term. If not, the process may flow to a decision block 118. In the decision block 118, the data processing system 38 may determine whether the most recently updated location data 34 includes location data 34 from the HL7-based system 30. If so, in step 120, the data processing system 38 may resolve the precise location 74 of the patient as the location data 34 associated with the HL7-based system 30, since the HL7-based system 30 may be the next most reliable source of location data 34 in the short term. If the location data 34 does not include recently updated data from the security access system 78 or the HL7-based system 30, the most recently updated data may derive from the RTLS 28.

Though the RTLS 28 location data 34 may be more recently updated, the RTLS 28 location data 34 may not be as precise as the HL7-based system 30 location data 34 or the security access system 78 location data 34. As such, the data processing system 38 may continue to resolve the precise location 74 of the patient in the process 112, starting with step 122. In step 122, the data processing system 38 may define location data 34 from each system 28, 30, or 32 as "assigned" or "current," and may further prioritize the location data 34 of each definition. For example, the HL7-based system 30 location data 34 may be defined as "assigned," since such location data 34 was most likely entered manually by medical facility personnel. Meanwhile, the RTLS 28 location data 34 and/or location data 34 from other location systems 32, such as the security access system 78, may be defined as "current," since such location data 34 most likely correlates to an automatic reading of a current location. Due to varying levels of accuracy or precision associated with the location data 34 of each system 28, 30, or 32, location data 34 defined as "assigned" or "current" may further be prioritized. For example, if location data 34 from multiple systems 28, 30, or 32 are defined as "assigned," such location data 34 may be prioritized in order of precision. Alternatively, if location data 34 from multiple systems 28, 30, or 32 are defined as "current," such location data 34 may be prioritized in order of accuracy.

In step 124, the location data 34 may be mapped to a hierarchy of possible locations, such as the exemplary hierarchy 48 of FIG. 3. Thereafter, as illustrated by decision block 126, the data processing system 38 may determine whether the "assigned" location data 34 is consistent with the "current" location data 34. If so, because the "assigned" location data 34 may be more precise than the "current" location data 34, the data processing system 38 may resolve the precise location 74 as the most precise "assigned" location, as illustrated by step 128. If the "assigned" location data 34 is not consistent with the "current" location data 34, the data processing system 38 may resolve the precise location 74 as the most precise "current" location, as illustrated by step 130.

Technical effects of the invention may include, among other things, increased precision over real-time location systems (RTLS) and/or increased accuracy over static location systems such as Health Level Seven (HL7)-based location systems. Such improvements may enable a medical facility to accurately track a patient when a patient leaves an assigned location, while also providing a precise assigned location when the patient returns.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system comprising:
    a memory device having instructions stored therein;
    a processor configured to execute the instructions stored in the memory device, the instructions comprising to:
        receive a plurality of patient locations representing locations where a patient is identified as located in a medical facility, wherein the plurality of patient locations includes a first location deriving from a first location system and a second location deriving from a second location system, and wherein the first location system has greater precision than the second location system and the second location system has greater accuracy than the first location system;
        map each of the plurality of patient locations into a hierarchy of patient locations that describes parent-child relationships between discrete possible patient locations in the medical facility;
        determine whether the first location is a descendant of the second location in the hierarchy of patient locations;
        when the first location is the descendant of the second location in the hierarchy of patient locations, output the first location as a resolved patient location; and
        when the first location is not the descendant of the second location in the hierarchy of patient locations, output the second location as the resolved patient location.

2. The system of claim 1, wherein each of the plurality of patient locations respectively corresponds to exactly one location within the hierarchy of patient locations.

3. A computer-implemented method comprising:
    using a processor of a data processing system to:
        receive subject location data representing locations where a subject is identified as located in a medical facility, wherein the subject location data includes assigned location data from a static subject location system and real-time location data from a real-time subject location system, wherein the static location system has a greater precision than the real-time subject location system and the real-time location system has a greater accuracy than the static subject location system;
        relate the assigned location data and the real-time location data via a hierarchy of subject locations of the medical facility data;
        select as a resolved patient location the most precise accurate one of the assigned location data and the real-time location data based at least in part on the relationship between the assigned location data and the real-time location data in the hierarch of location data; and
        output the resolved subject location.

4. The computer-implemented method of claim 3, wherein using the processor of the data processing system to select as the resolved patient location the most precise accurate one of the assigned location data and the real-time location data comprises determining whether the assigned location data is accurate, wherein the static location data is determined to be accurate when a subject location represented by the assigned location data is a descendant of a subject location represented by the real-time location data in the hierarchy.

5. The computer-implemented method of claim 4, wherein using the processor of the data processing system to select as the resolved patient location the most precise accurate one of the assigned location data and the real-time location data comprises selecting the assigned location data as the resolved subject location when the assigned location data is accurate.

6. The computer-implemented method of claim 4, wherein using the processor of the data processing system to select as the resolved patient location the most precise accurate one of the assigned location data and the real-time location data comprises selecting the real-time location data as the resolved subject location when the assigned location data is not accurate.

7. The computer-implemented method of claim 3, wherein using the processor of the data processing system to select as the resolved patient location the most precise accurate one of the assigned location data and the real-time location data comprises selecting the resolved subject location based at least in part on when the assigned location data and the real-time location data were updated.

8. The computer-implemented method of claim 3, wherein the subject is a patient.

9. A method comprising:
   using a processor of a data processing system to perform:
   ascertaining an assigned patient location of a first granularity from an admissions/discharge/transfer system;
   ascertaining a real-time patient location of a second granularity from a real-time location system;
   receiving the assigned patient location and the real-time patient location into the data processing system;
   selecting as a resolved patient location the most precise accurate one of either the assigned patient location or the real-time patient location based at least in part on a hierarchy of patient locations stored on the data processing system; and
   outputting the resolved patient location.

10. The method of claim 9, wherein the real-time patient location system employs the Global Positioning System.

11. The method of claim 9, wherein the real-time location system comprises location data from a security access system.

12. The method of claim 9, wherein the resolved patient location is selected as either the assigned patient location or the real-time patient location based at least in part on when the assigned patient location and the real-time patient location were updated.

13. The method of claim 12, wherein selecting as the resolved patient location either the assigned patient location or the real-time patient location comprises selecting the real-time location when the real-time location has been updated a predetermined amount of time more recently than the assigned location and neither the assigned location nor the real-time location are descendants of each other in the hierarchy.

* * * * *